United States Patent [19]
Albright et al.

[11] 3,963,349
[45] June 15, 1976

[54] METHOD AND APPARATUS FOR DETERMINING COAGULATION TIMES

[75] Inventors: Bill E. Albright, Hialeah; Stephen M. Meginniss, III, St. Petersburg, both of Fla.

[73] Assignee: American Hospital Supply Corporation, Evanston, Ill.

[22] Filed: Aug. 27, 1974

[21] Appl. No.: 500,910

[52] U.S. Cl. .................................. 73/64.1; 356/36; 356/201; 356/244; 23/230 B; 23/253 R; 356/39
[51] Int. Cl.$^2$ ................. G01N 33/16; G01N 21/16; G01N 31/00
[58] Field of Search ................ 356/36, 39, 40, 196, 356/201, 244, 246; 23/230 B, 253 R; 73/64.1

[56] References Cited
UNITED STATES PATENTS

| | | | |
|---|---|---|---|
| 3,267,362 | 8/1966 | Page | 23/230 B |
| 3,814,585 | 6/1974 | Bailly | 356/39 |

Primary Examiner—Vincent P. McGraw
Assistant Examiner—Jon W. Henry
Attorney, Agent, or Firm—Dawson, Tilton, Fallon & Lungmus

[57] ABSTRACT

A method and apparatus for determining coagulation times in such clinical laboratory procedures as prothrombin time tests, activated partial thromboplastin time tests, fibrinogen determinations, factor assays for specific blood coagulation factors, and the like. A fibrous filament is drawn at a predetermined rate through a small body of liquid to be tested and the interval, from the time a suitable coagulating agent is mixed with the liquid to the time the body of liquid clings to the filament and moves with it, is precisely measured as a direct indication of actual coagulation time. The liquid body is supported upon a nonwettable inclined surface bordered by walls defining a well for receiving the liquid and a pathway for its movement. Particularly effective results are achieved by utilizing a pair of spaced filaments moving at precisely the same rate, the filaments being bridged by a web or mass of clotted liquid when coagulation occurs. A photodetector senses movement of the clot and a timer automatically measures the time between coagulant addition and clot formation. After clot detection occurs, an arm lifts the paired filaments from the well while at the same time directing the advancing filaments through slots to strip coagulum therefrom, then lifts the filaments out of the slots to permit fresh filament sections to move into place, and finally lowers the fresh sections onto a clean inclined surface for another coagulation test. Means are also disclosed for gently agitating the coagulating agent or agents prior to admixture with the test liquid, for insuring proper suspension of the reactants, and for reducing risks of infection and cross contamination during use of the apparatus.

40 Claims, 17 Drawing Figures

METHOD AND APPARATUS FOR DETERMINING COAGULATION TIMES

BACKGROUND

Two basic objectives for any device intended for automatic measurement of coagulation times are, first, that an established endpoint in the coagulation process be precisely and immediately detected so that significant reproducible results will be obtained and, second, that there be no cross contamination or carry-over from one sample to the next. While some devices known in the past have satisfied the first of these objectives, and others the second, such devices have generally failed to achieve both. Thus, electrical coagulation detectors which measure changes in conductivity (resistance) as an indicator of clot development, and optical detectors which respond to changes in reflected or transmitted light, may present relatively few carry-over or contamination problems but, unfortunately, they generally lack precision, reliability, and reproducibility in endpoint detection. On the other hand, mechanical or electro-mechanical detectors, which usually include immersible elements and which respond more directly to changes in viscosity, are more precise in endpoint detection but clearly present substantial carry-over problems.

An early method for measuring the coagulation time of freshly-drawn whole blood was that of H. Vierordt [1878, Arch. f (physiologische) Heilkunde Vol. 19] who disclosed drawing a natural filament (a meticulously cleaned white horse hair) through a glass tube containing raw blood and determining the coagulation endpoint by observing when the filament became reddish (because of red cells clinging thereto) or the coagulum (fibrin) attached itself to the moving filament. In 1910 K. Kottmann and A. Lindsky [Zeitschzift fur Klinische Medizin 69:431–434 (1910)] modified Vierordt's method by incorporating thermoregulation, and in 1921 R. Schmidt [Medizinisch Klinik 17. Jahrgang Nr. 16, 439–60 (1921)] altered the thermoregulation aspect by using a U-tube instead of the straight tubes used by Vierordt and by Kottmann and Lindsky.

While Vierordt's approach may still be suitable for so-called global assays in which the coagulation time of freshly drawn whole blood is determined, and in which the coagulation time is measured in minutes, it is not suitable for the more specific coagulation tests, such as prothrombin time tests and activated partial thromboplastin time tests, where results are measured in seconds, and even in fractions of seconds, following the addition of a coagulating agent to a plasma sample. Despite considerable activity in this field, prior efforts have failed to produce a precise and reliable automatic method for measuring coagulation times, particularly for the specific assays so widely used in clinical laboratories.

The following references, and the citations therein, further indicate the state of development of the prior art: U.S. Pat. Nos. 3,766,774, 3,658,480, 3,605,010, 3,267,364, 3,268,804, 3,704,099, 3,267,363, 3,020,748, 3,077,106, 3,038,327, 3,518,057, 3,560,162, 3,525,254, 3,458,287, and 3,492,096.

SUMMARY OF INVENTION

This invention is concerned with a method and apparatus capable of achieving both of the objectives described above and, therefore, of overcoming the aforementioned limitations and deficiencies of prior methods and equipment.

In the best mode presently contemplated for carrying out the invention, the apparatus includes a tray having a plurality of adjacent recesses, each recess including a well portion and an inclined pathway or ramp. The well and ramp have a common bottom surface composed of a superhydrophobic material consisting of fumed silica microparticles. A pair of parallel fibrous filaments are supported so that they may be drawn through the well and along the ramp or pathway (slightly above the surface thereof) at the same precisely controlled rate. A drop or small body of clottable liquid to be tested (i.e., blood or plasma) is placed into the well, a coagulating agent is admixed therewith, and filament movement is commenced. The body of liquid gels until finally the forces of attraction between the moving filaments and the body exceed the resistance to movement of the body along the upwardly sloping ramp. As the clotting endpoint is reached, the body commences to move along with the filaments and such movement is detected photoelectrically as the clot, with the bulk of its mass spanning the two filaments, moves into the path of a light beam. The interval between addition of the coagulating agent and the interruption of the beam is directly representative of the clotting time of the sample.

The clot is automatically stripped from the stretches of filament upon movement of a support arm which lifts the trailing portions of those stretches while permitting the leading portions thereof to pass through a pair of grooves in a barrier wall. Upon engagement with the wall, the clot is stripped from the filaments and is collected in a trough. Thereafter, the leading portions of the filament stretches are also lifted and cleaned filaments are advanced onto a takeup reel assembly. As fresh filament sections of stretches move into position, a second sample, supported in an adjacent recess of the tray, is indexed beneath the clean filament stretches, the filaments are lowered, and the process is repeated.

Accurate positioning of the filaments in relation to a fluid sample is achieved in part by passing those filaments through guide notches or grooves at opposite ends of each tray recess, and precise control over the rate of movement of such filaments is achieved by exerting a constant pulling force by means of take-up reels which are power driven through slip clutches, and by feeding the filaments through a constant-speed capstan assembly which is disposed in advance of the recess and which operates at a lower speed than the take-up reels. During clot-stripping or tray-indexing operations, the filaments are permitted to disengage from the capstan and move forwardly at the greater unrestrained speed of the take-up reels.

The take-up reel assembly includes a drip pan which is connected to the reels, the entire assembly being detachable from the remainder of the apparatus so that the pan and loaded reels may be discarded as a unit. Problems of contamination which might otherwise arise from direct contact with sample fluids may therefore be easily avoided.

Each coagulating agent is supported in a reagent cup and is automatically transferred by a pipetting mechanism from that cup to the sample contained in a well of the tray at the commencement of a test sequence. Gentle agitation of the material in the reagent cup is achieved by oscillating the cup while the pipette tip of the transfer mechanism projects into the contents of that cup. The pipette tip therefore serves both as a transfer device and as a stirring element. It has been found that such a system is highly effective in maintaining the various components in suspension without inactivating the more delicate or highly sensitive reagents.

The apparatus and method disclosed in this application, as representing the best mode for practicing the invention (as specifically claimed herein) of which applicants are presently aware, are also disclosed in co-owned application Ser. No. 500,911, filed on the same date in the name of Mario Theodore Geiger.

Other advantages and objects of the invention will become apparent as the specification proceeds.

DETAILED DESCRIPTION

Referring to the drawings, the numeral 10 generally designates an apparatus embodying the present invention, the apparatus including a casing 11 having a top panel 12, vertical front and side panels 13 and 14, a sloping control panel 15 and a removable cover 15a (a portion of which is shown in phantom and may, if desired be formed of transparent material). An array of control buttons 16 is located along the control panel, the number and purpose of such buttons being variable depending on the particular type of coagulation tests which the apparatus is adapted to perform. For clinical laboratory use, the apparatus may be programmed to conduct prothrombin time (PT) tests, activated partial thromboplastin time (APTT) tests, fibrinogen determinations, factor assays for blood coagulation factors II, V, VII, VIII, IX, X, XI, and XII, and identification and plasma assays. Since the circuitry and details of the programming constitute no part of this invention, further discussion of the controls is believed unnecessary herein.

Figures 9, 10:
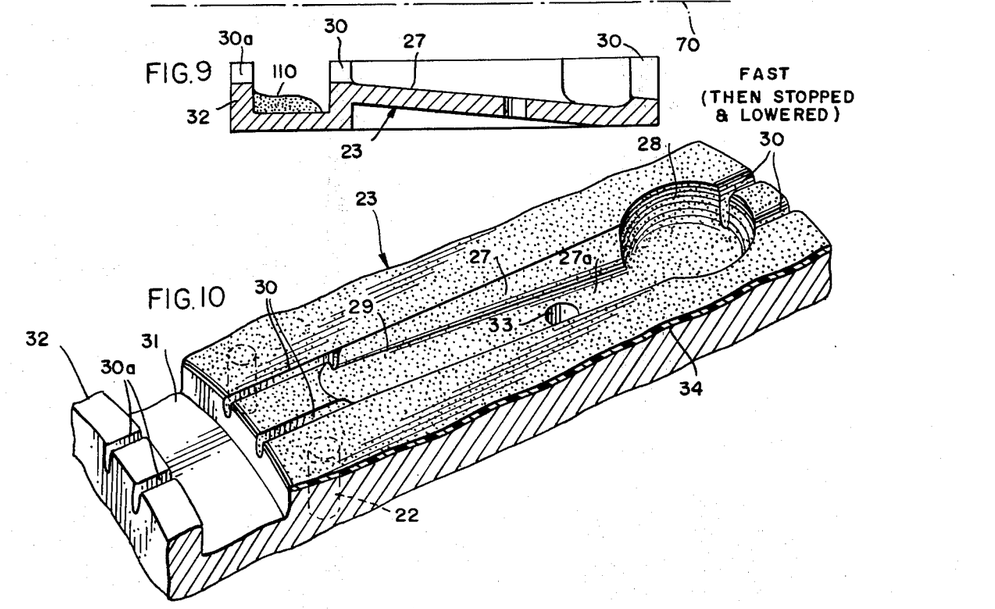
FIG. 10 is an enlarged fragmentary perspective view illustrating a portion of a sample tray.
Figure 13:
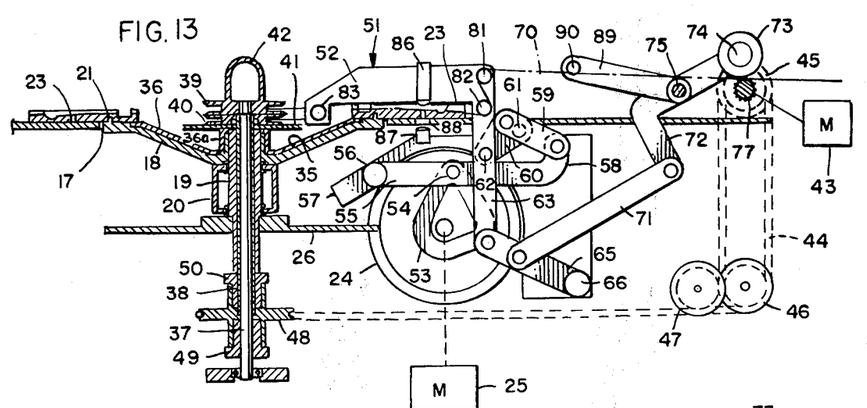
FIGS. 13-15 are somewhat schematic sectional views illustrating the relationship of parts of the apparatus during coagulation time measurement (FIG. 13), during removal of a clot from the filament (FIG. 14), and during indexing of the turntable and further advancement of the filament (FIG. 15).

The top panel is provided with a central opening 17 in which is located a turntable 18 carried by sleeve 19 which is in turn journaled in rigid frame members 20 (FIG. 13). The upper peripheral surface of the turntable is provided with a series of upstanding circumferentially spaced pins 21 adapted to be received in openings 22 (FIG. 10) in the undersides of arcuate trays 23 for releasably supporting the trays upon the turntable for rotation therewith. It will be observed from FIG. 13 that the upper surface of the turntable is flush with the top panel 12 and that arcuate trays 23 project outwardly beyond the turntable and are slidably supported directly by the top surface of panel 12. Such a construction is advantageous because it assures precise orientation of the trays with respect to the top surface and because the direct contact between the trays and top panel permits the direct transmission of heat for maintaining the trays at proper temperature for conducting the tests, such heat being supplied by suitable heating means within the casing directly below top panel 12 (not shown).

The turntable is indexed in one direction by a stepping cam 24, driven intermittently by motor 25, which has its peripheral edge received in the notches between the teeth of wheel 26 secured to sleeve 19. Any other suitable intermittent drive mechanism, all as well known in the art, may be used for indexing turntable 18 and the trays 23 connected thereto.

In the particular embodiment illustrated in the drawings, each tray 23 is provided with a plurality of adjacent recesses 27 having bottom surfaces 27a which slope upwardly and inwardly. Each recess is enlarged at its outer end to define a well portion 28, the well communicating directly with the narrower sloping pathway 29 and bottom surface 27a being common to both portions. As shown most clearly in FIG. 10, a pair of parallel grooves 30 are formed in the top of the tray along each recess 27, the grooves communicating with well 28 and pathway 29 for the purpose of guiding a pair of filaments in precisely spaced relationship through each recess 27. Also, since the grooves or notches 30 have their lower ends terminating above the bottom surface 27a of the recess, such grooves contribute in precisely maintaining the filaments at a slight but definite distance above that surface.

Each tray is provided along its inner edge — that is, the edge closest to the axis of the turntable — with a trough on channel 31 bordered by an upstanding inner barrier wall 32 having notches or grooves 30a aligned with the grooves 30 communicating with recess 27. Within each recess is a vertical passage 33 dimensioned and arranged to permit the passage of light therethrough without allowing the escape of coagulated fluid. The surface of each recess, and preferably the top portion of the tray adjacent each recess, is coated at 34 (FIG. 10) with a suitable hydrophobic material. While waxes, silicone, and other non-wetting materials might be suitable, it has been discovered that silane-treated fumed silica, available as Silanox from Cabot Corporation of Boston, Massachusetts is uniquely effective because of its superhydrophobicity, the uniformity of that hydrophobicity, the hardness of the coating, and the temperature stability of the coating layer. Unlike other hydrophobic surfaces, the silica-treated surface comprises a multiplicity of fumed silica microparticles which provide a macroscopically smooth (and hence referred to herein as generally smooth) but microscopically uneven support for the body of fluid. Such body is supported and rides only upon the projecting tops of the fumed silica particles to greatly reduce contact area and resistance to movement of the body along the non-wettable surface.

Referring to FIG. 13, it will be observed that turntable 18 is dish-shaped, having a downwardly and inwardly sloping wall portion which defines an upwardly facing annular recess 35. A removable and disposable drip pan 36 lines the recess and, as shown in the drawings, is provided with an upstanding collar 36a which extends about the hub portion of the turntable. While the liner may be formed of any suitable material, plastics such as polystyrene or polypropylene are believed particularly effective.

Figure 16:
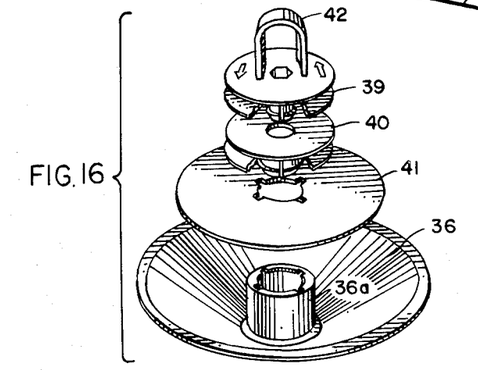
FIG. 16 is an exploded perspective view illustrating the disposable take-up reel and drip pan assembly.

A pair of coaxial shafts 37 and 38 are journaled in sleeve 19 of the turntable. The upper ends of the shafts project above the plane of top panel 12 and are non-circular (i.e., hexagonal) in configuration. A pair of reels 39 and 40 are removably fitted upon the upper ends of shafts 37 and 38, respectively, and a disk-shaped shield 41 is interposed between the reels and the upstanding collar 36a of the liner or drip pan 36. Like the drip pan, reels 39 and 40 and shield 41 may all be formed of plastic materials and are therefore disposable by incineration. The entire drip pan and take-up reel assembly is illustrated in exploded perspective view in FIG. 16. Interconnection of the parts to provide a unitary assembly is achieved by providing upper reel 39 with a notched depending flanged sleeve 39a which is snap fitted into opening 40a of lower reel 40. Similarly, the lower reel is provided with a depending flanged and notched sleeve 40b which extends through central opening 41a in the shield and into opening 36b at the upper end of collar 36a of the drip pan 36. The flanged sleeves prevent axial separation of the parts without preventing independent relative rotation of those parts. Preferably, the upper reel 39 is provided with a handle 42 to facilitate removal of the entire drip pan and reel assembly when replacement is required.

As already described, upper reel 39 is carried by shaft 37 and lower reel 40 is carried by shaft 38. The two shafts are driven by a motor 43 with power transmitted by a belt 44 entrained about pulleys 45–48. Pulley 48 is associated with slip clutch assemblies 49 and 50 of conventional construction. Because of the slip clutch assemblies, the rotational speed of the reels 39 and 40, and the shafts on which they are mounted, may be reduced by reason of load resistance without slowing belt 44 or motor 43.

Figure 14:
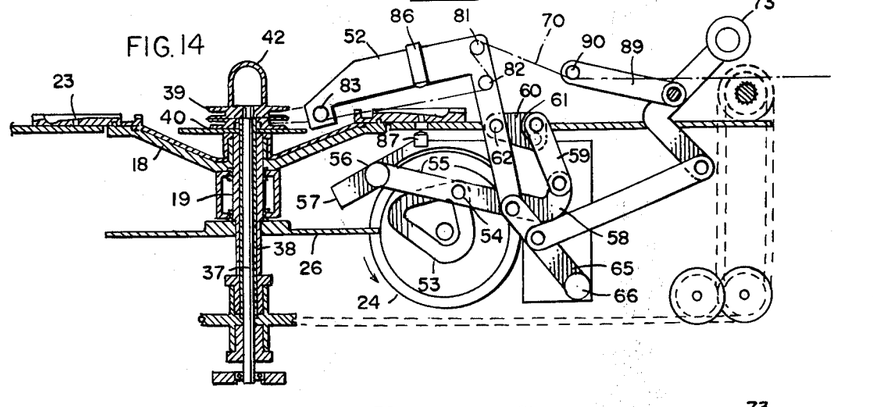
Figure 15:
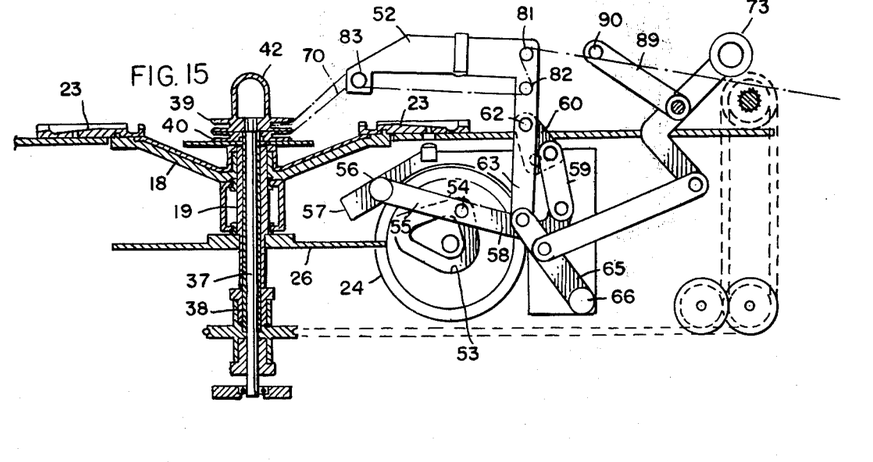

The indexing or stepping cam 24 (FIGS. 13–15) not only advances turntable gear 26 an angular distance equal to the width of a gear tooth each time the cam executes one revolution, but also cooperates with a guide arm assembly 51 to shift arm 52 into each of the three positions illustrated in FIGS. 13–15. Specifically, the face of cam 24 is provided with a groove 53, and a rider 54, carried by link 55, travels in the groove as the cam rotates. Link 55 is pivotally connected at one end 56 to frame member 57; thus, as the cam rotates, the opposite end 58 of link 55 swings upwardly and downwardly into the positions illustrated. End 58 of link 55 is connected to link 59 which is in turn connected to link 60. Link 60 is pivotally mounted on the frame at pivot point 61 and is also connected at point 62 to the depending portion 63 of guide arm 52. The depending extension 63 of the guide arm is pivotally connected to link 65, the latter being connected to the frame at pivot 66. The result is that as the indexing cam rotates, the main portion of guide arm 52 disposed above top panel 12 and turntable 18 shifts between a lowered first position (FIG. 13) in which it is generally horizontal and is in close proximity to a tray supported by the turntable, an inclined second position (FIG. 14) in which its free end remains lowered but its rear portion lifts upwardly away from the tray, and a raised third position (FIG. 15) in which the arm is again horizontal but is spaced well above the turntable and tray.

The guide arm assembly 51, including its link arrangement, is coordinated with means for precisely controlling the rate of movement of fibrous filaments 70 and for intermittently permitting rapid advancement of those filaments. Referring to FIG. 13, it will be noted that link 71 extends between link 65 and one end of an L-shaped roller support member 72. A resilient roller 73 is carried by a horizontal shaft 74 at the free end of the support member and, as shown most clearly in FIGS. 3 and 13, that member is mounted for tipping movement (as link 65 is raised and lowered) by horizontal bar 75 secured to a pair of upstanding flanges 76.

Figure 3:
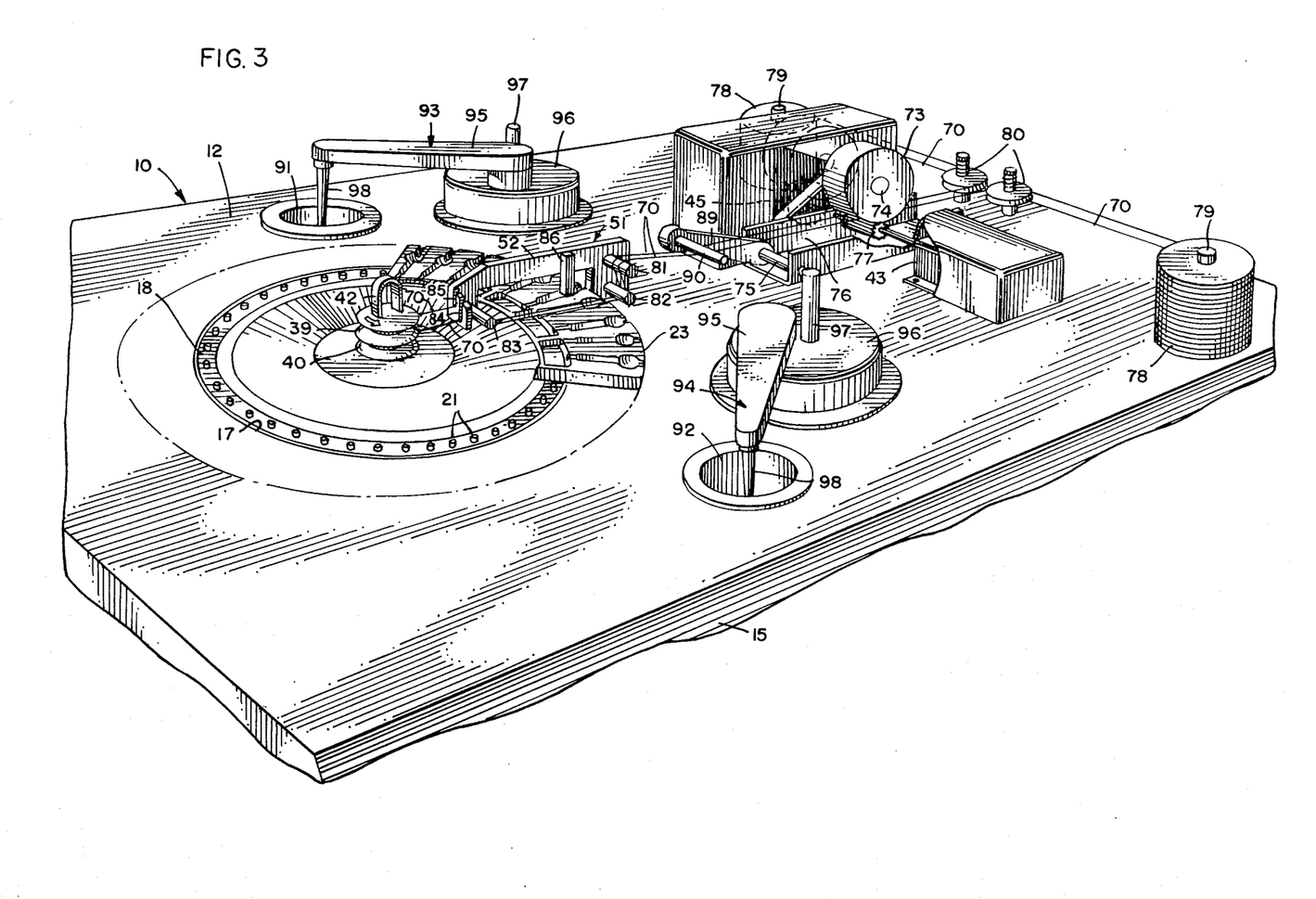
FIG. 3 is an enlarged fragmentary perspective view showing portions of the thread advancing, supporting and guiding mechanisms, the detector assembly, and the sample supporting surface, and other components disposed immediately beneath the top panel of the casing.

As the roller support arm pivots about shaft 75, the resilient roller 73 is shifted between a lowered position (FIG. 13), in which its periphery is in direct contact with the knurled shaft or capstan 77, and a raised position wherein the roller and shaft are spaced apart (FIGS. 14 and 15). Shaft 77 is power driven at constant speed and, in the embodiment illustrated, constitutes a portion of the shaft of motor 43 (FIG. 3). Pulley 45 is mounted upon an extension of that same shaft and, as previously described, the pulley 45 and belt 44 operate at constant speed regardless of rotational resistance imposed on take-up reels 39 and 40.

Referring to FIG. 3, filaments 70 are supplied by a pair of spools 78 supported upon upstanding spindles 79. The filaments pass between the plates of spring tensioners 80 and then towards take-up reels 39 and 40. Guide arm 52, and resilient roller 73 and shaft 77, are interposed between the take-up reels 39–40 and the tensioning elements 80. The driving force for advancing the filaments is transmitted by the take-up reels and the rate at which such reels advance the filaments, in the absence of a restraining force capable of causing clutches 49 and 50 to slip, is greater than the peripheral speed of the shaft or capstan 77. Consequently, when resilient roller 73 is lowered to force filaments 70 into firm engagement with shaft 77, the rate of advancement of the filaments is controlled or metered by constant-speed shaft 77. When roller 73 is raised, the filaments are again free to advance at the full rate capable of being produced by power-driven take-up reels 39 and 40. It is to be noted that when resilient roller is raised, thereby rendering the shaft 77 inoperative to control or meter the rate of travel of the filaments, the speed of advancement of such filaments will vary slightly depending on the extent of material already wound upon the take-up reels, but that when the resilient roller is lowered and the rate of filament advancement is controlled by constant-speed shaft 77, the travel of the filaments is not only substantially slower but is maintained precisely at a uniform predetermined level.

Arm 52 bridges the tray-supporting portion of the turntable and is provided with lateral guide bars or members 81–83 for guiding the paired filaments over the recess of a tray and for urging the filaments into the paired grooves or notches 30 at opposite ends of that recess. At the forward end of the guide arm 52 are a pair of upwardly projecting fingers defining slots 84 and 85 for guiding each thread towards its respective take-up reel. Intermediate the front and rear ends of the generally horizontal arm 52 is a light source 86 positioned to align precisely with one of the vertical openings 33 in the recessed bottom surface of a tray (FIG. 10) when the arm is in the lowered position shown in FIG. 13. A photocell 87 (FIGS. 13 and 17) disposed in vertical alignment with light source 86, is mounted on frame 57, the top panel 12 of the casing being provided with an aperture 88 in register with the light source and photocell to permit the beam of light to pass directly between the source and the beam of light to pass directly between the source and the photocell.

To avoid slack in the filaments regardless of arm movement or position, a tensioning force is applied to the filaments at all times. The tensioning member consists of a bar 89 pivotally connected at one end to shaft 75 for swinging movement in a vertical plane and provided at its opposite end with a lateral finger element 90 which rests upon both filaments (FIG. 3). The weight of the bar and its lateral member exerts a downward force on the filaments 70 to maintain the filament stretches between take-up reels 39–40 and spring resistance devices 80 under a desired degree of tension.

Figure 1:
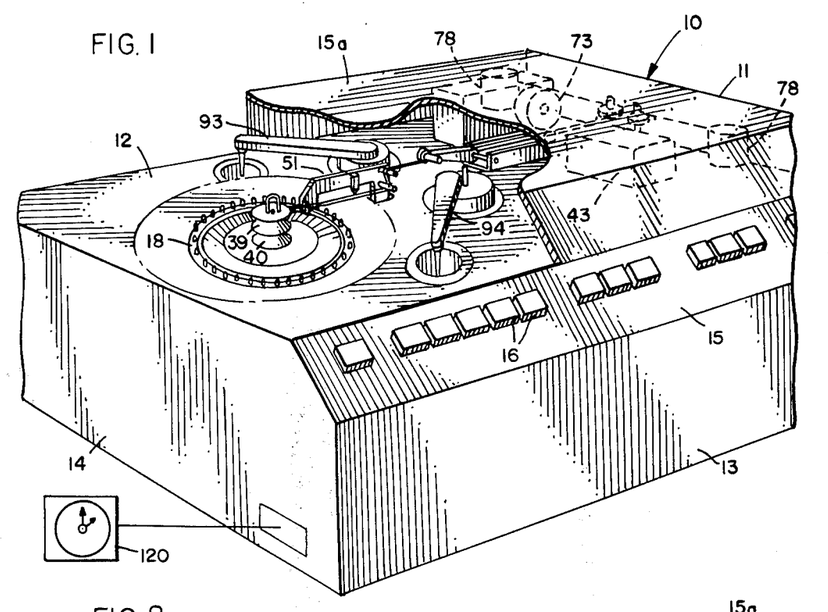
FIG. 1 is a perspective view of an apparatus embodying the invention, the apparatus casing being partly broken away to reveal internal components.
Figure 2:
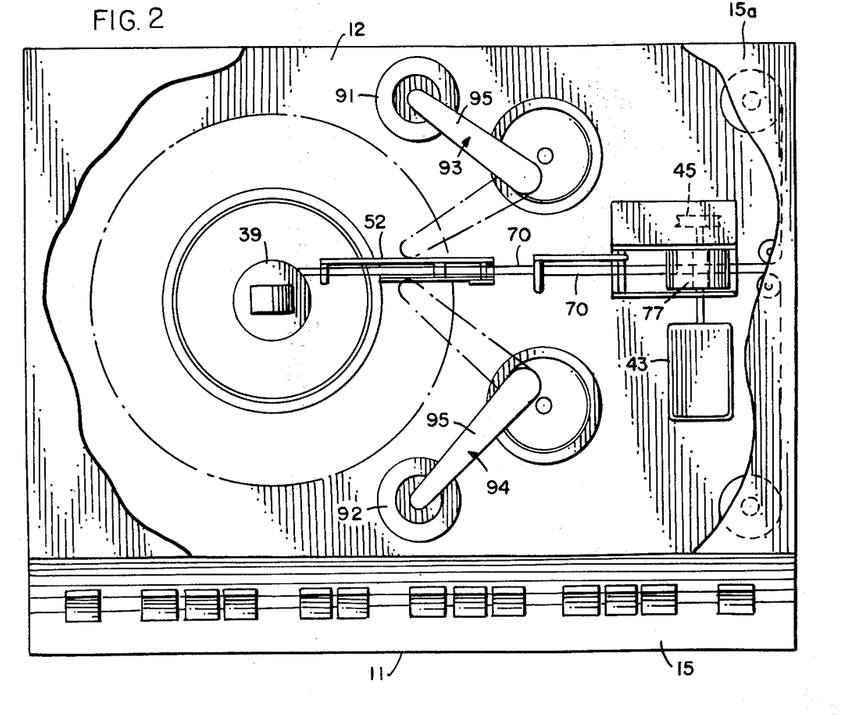
FIG. 2 is a somewhat diagrammatic top plan view of the apparatus illustrating the relationship of parts.

The addition of fluids to the wells 28 of the trays may be automatic, semi-automatic, or manual, although it has been found that a semi-automated operation, wherein the test samples are manually placed in a tray and the subsequent addition of one or more reagents is performed automatically by the apparatus, is particularly effective. Referring to FIG. 3, a pair of reagent cups 91 and 92 are disposed adjacent opposite sides of the turntable and delivery means 93 and 94 are provided for transferring measured amounts of reagent from one or both cups to the well of a tray disposed beneath arm 52. Each transferring means includes a pipetting arm 95, mounted on a power-operated turret for vertical movement along a spindle 97 and for horizontal rotation between the mixing withdrawing position illustrated in FIGS. 1–3 and the dispensing position illustrated in broken lines in FIG. 2. Since the turret construction constitutes no part of the present invention, and since any of a number of well known mechanisms might be used for automatically transferring reagents from the cups to the wells of the trays, and further, since such operations might be performed manually, discussion of the details of the transfer mechanism and its operation is believed unnecessary herein.

It should be noted, however, that FIG. 3 illustrates each pipetting arm 95 in a normal rest position with its pipetting tip 98 extending downwardly into an open-topped cup 91 (or 92). In that position, the pipetting tip is not only ready to draw a measured amount of reagent, but also serves as a stirrer for gently mixing the contents of each cup. Such mixing occurs not because of movement of the pipette tip, but because of oscillation of the cup while the stationary pipette tip projects downwardly into the contents of that cup.

Figure 17:
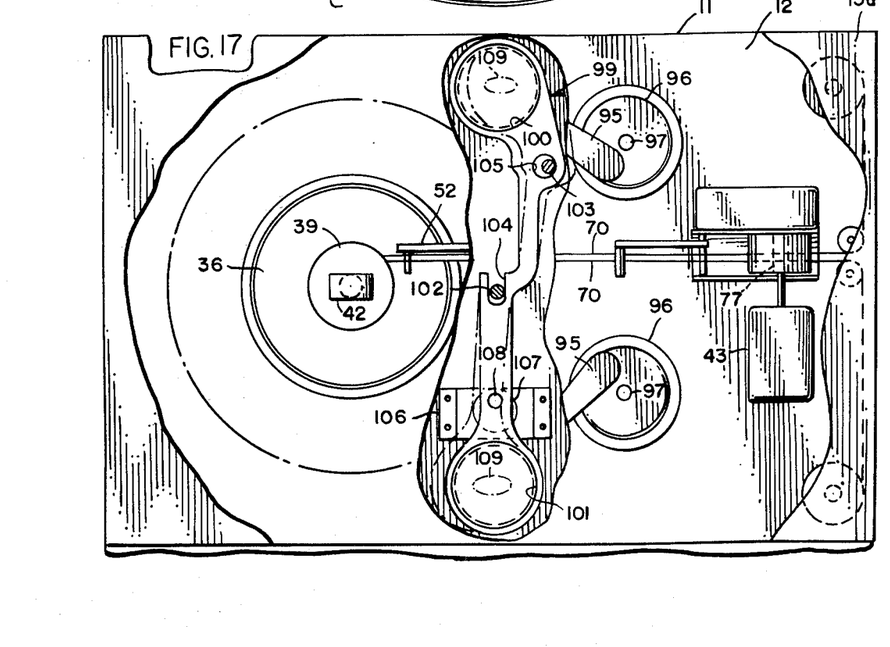
FIG. 17 is a fragmentary plan view illustrating the reagent receptacles and the means for gently agitating their contents.

The oscillating mechanism is shown in FIG. 17. A cup support bar or member 99 extends horizontally beneath top panel 12 and is provided at opposite ends with openings 100 and 101 for removably receiving cups 91 and 92. Horizontal movement of the member is limited by pins 102 and 103, both of which are rigidly secured to panel 12. Pin 102 is centrally disposed between the cups and is received within a slot 104 whereas pin 103 is disposed intermediate the central point and one of the cups (91) and is loosely received within enlarged opening 105. Adjacent the opposite end of the member is a motor 106 with a disk 107 rotated by its drive shaft. The disk is provided with an eccentric pin 108 journaled in a portion of member 99 adjacent cup-receiving recess 101. As the motor operates, eccentric shaft 108 causes each cup recess 100 and 101, and the cups disposed therein, to execute an elliptical orbit represented in FIG. 7 by broken lines 109. Consequently, a relatively gentle and highly effective stirring action is achieved during operation of the apparatus by the oscillatory movement of the cups and their contents with respect to the temporarily stationary pipette tips 98 projecting downwardly into the cups.

In operation of the apparatus, a technician first places a small quantity of blood, plasma, or other fluid capable of coagulating, into one or more wells 28 of an arcuate tray 23. The tray is then placed upon turntable 18 so that as the turntable indexes forwardly a recess containing a test sample will move into position beneath arm 52. The arm lowers into the position illustrated in FIG. 3, with the paired filaments fitting into grooves 30 to the full depth of those grooves.

Figures 4, 5:
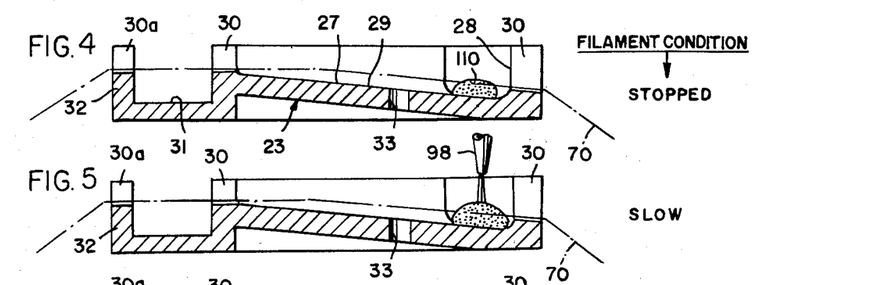
FIGS. 4-9 are schematic views illustrating the sequence of steps in the operation of the apparatus.

The sequence of operation is schematically illustrated in FIGS. 4–9. The body of clottable fluid is designated by the numeral 110 and, as shown in FIG. 4, that fluid body, which is ordinarily of the order of one or two drops in volume, rests on the smooth non-absorbent, and hydrophobic surface of well 28. The paired filaments extend through the well and through the body of fluid, but such filaments remain stationary until the coagulation process is initiated.

Inititation of the process leading to coagulation occurs upon the addition of a suitable coagulating agent. Where more than one agent is to be added, the one that is added last should be the coagulating agent. Thus, in a partial thromboplastin time test, two reagents are used, first a cephaloplastin reagent and then a calcium chloride reagent, the latter being regarded as the coagulation initiator. Such reagents are stored within the receptacles or cups 91 and 92, are agitated by oscillation of those cups relative to pipette tips 98, and are transferred to the well 28 by transfer mechanisms 93 and 94. FIG. 5 illustrates pipette tip 98 at the instant it discharges a measured quantity (typically 0.1 milliliter) into a well 28 and directly into the body of clottable fluid 110 contained therein. The discharge should be forceful enough to promote mixing of the reactants.

The instant such discharge and mixing takes place, motor 43 is energized and take-up reels 39 and 40 commence drawing the fibrous filaments through the fluid mixture. Precise control of the rate of movement of such filaments is achieved by knurled shaft 77, which serves as a throttling capstan, and resilient roller 73 which maintains the filaments in contact with the knurled shaft.

Figures 6, 7:
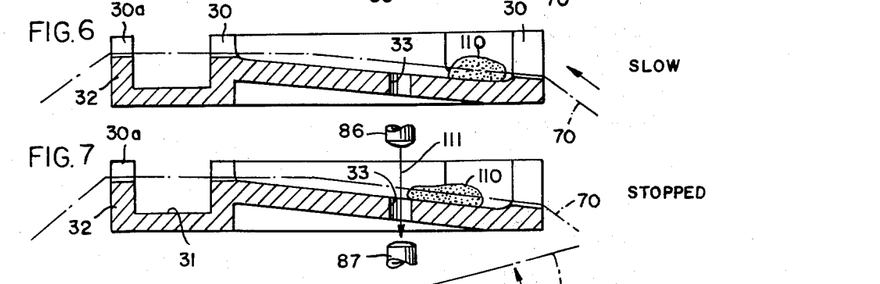

Movement of the filaments continues at a constant rate, as schematically depicted in FIG. 6, until a clot develops, clings to the filaments, and advances up the inclined pathway beyond the edge of opening 33 (FIG. 7). The instant that light beam 111 is interrupted by the clot, thread movement is stopped and the interval from the beginning to the end of such movement is measured as a direct indication of the clotting time for the sample. Preferably the interval is measured, displayed, and recorded by any suitable timing and recording devices as well known in the art, such a device being diagrammatically represented in FIG. 1 and designated by numeral 120.

Figure 11:
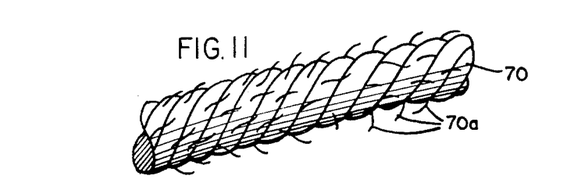
FIG. 11 is a magnified perspective view illustrating the fibrous nature of the filament.

In the operation of the apparatus, the use of filaments of fibrous character has been found particularly important. The fibrous nature of a typical filament 70 is illustrated in FIG. 11, such filament being shown in greatly magnified condition. Various grades of cotton thread have been found effective for this purpose, but filaments formed of other fibrous materials should also be suitable. By fibrous, it is meant that the filament is formed of a multiplicity of fibers which are twisted together and which have hair-like end portions 70a projecting from the body of the filament. Such projections are not only believed to play an important part in the attachment of a clot to the filament, but also promote more complete mixing of the reactants during the test procedure.

Figure 12:
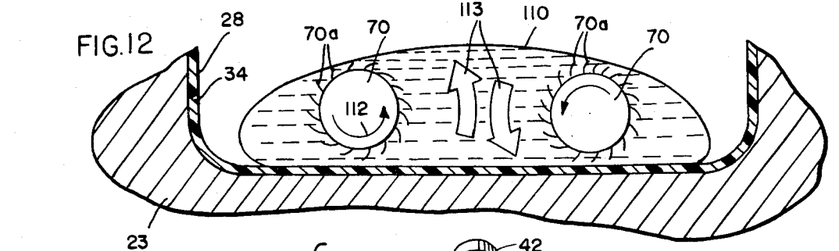
FIG. 12 is a magnified and somewhat schematic sectional view depicting the manner in which the filaments promote mixing of a sample with the reagent which activates coagulation.

FIG. 12 schematically illustrates how such mixing is promoted. It has been found that as the twisted filaments advance, a rotational movement occurs as indicated by arrows 112. Such rotation takes place because such filament is being drawn over and about various guides as it travels from supply spool 78 to take-up reel 39 (or 40). The rotation of the filaments induces movement within fluid body 110 in the manner indicated by arrows 113. The mixing action caused by such filament rotation is enhanced where two filaments are used because, as shown in FIG. 12, the fluid is forced in opposite directions within the central zone of the body 110.

While blood, plasma, or other clottable fluids are capable of clinging to a single filament when a clot is developed, the use of paired filaments is important because more precise control over clot movement and orientation can be achieved. Specifically, as the clot develops, the bulk of its mass is disposed between the spaced filaments. The light source 86 of the detector system directs its beam between the filaments and through opening 33. Consequently, the beam is directly in the path of the major portion of a clot pulled along by the spaced filaments. In determinations where fractions of a second are meaningful, the precision and reproducibility achieved by a two-filament arrangement are of considerable significance.

Figure 8:
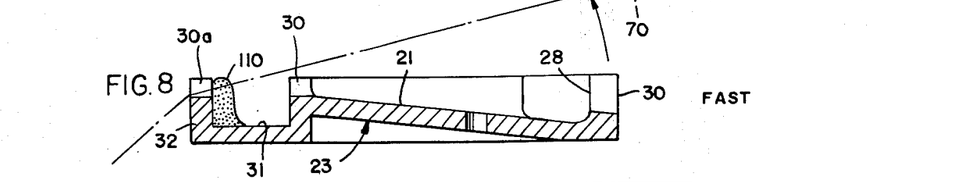

After the clot has been detected, motor 25 drives timing cam 24 through one complete revolution. As cam movement commences, the rear end of arm 52 is lifted so that filaments 70 assume the inclined condition shown in FIG. 8. During the lifting operation, resilient roller 73 is removed from capstan 77 (FIG. 14) so that the take-up reels 39 and 40 may advance the filaments at a relatively rapid rate without the restraint previously imposed by the capstan. While the inclined filaments are shown in FIG. 8 to be lifted free of grooves 30 at both ends of the recess 27, the slope of the filaments may be reduced, if desired, so that such filaments clear the grooves adjacent well 28 but still pass through the grooves 30 adjacent channel 31. In any event, the inclined filaments must pass through grooves 30a in inner wall 32 of the tray. The result is that the clot carried by the filaments is lifted free of the recess, any liquid supported by the filaments tends to drain downwardly along those filaments (and away from the fresh uncontaminated filament stretches therebehind), and the gelatinous mass is rapidly advanced toward channel 31 where it is stripped off of the filaments by the grooved inner barrier wall 32 (and by that wall portion providing grooves 30 adjacent the channel 31 in those constructions in which the inclined filaments may continue to pass through those grooves).

In the final stage of the operation, indexing cam 24 is rotated to a point where the front portion of the guide arm 52 is also lifted (FIG. 15). The indexing cam engages the next tooth of indexing gear 26 to rotate the turntable and the tray beneath the raised filaments. The filaments continue their rapid advance until fresh sections of the paired filaments are brought into position above the next recess in the tray, the arm 52 and filaments 70 supported thereby are then lowered into the position illustrated in FIG. 4, and the entire process is repeated.

While most of the coagulum is stripped from the filaments and deposited in the trough or channel 31 of the tray, some portion of it necessarily remains on the filaments and is carried toward the take-up reels. Should any fluid drip from the filament sections after they are lifted free from the tray and before they are wound upon the take-up reels, such material would be expected to be collected by drip pan 36. Finally, when the filament supply is exhausted from spools 78, or at any other convenient time, the entire take-up reel and drip pan assembly is lifted (by handle 42) from the apparatus and is discarded for disposal by incineration. An operator may therefore avoid direct contact with all of the fluids involved in the test procedure and thereby avoid dangers of contamination which might otherwise arise.

While in the foregoing, an embodiment of the invention has been disclosed in considerable detail for purposes of illustration, it will be understood by those skilled in the art that many of these details may be varied without departing from the spirit and scope of the invention.

We claim:

1. A method for determining the coagulation time of a fluid following the addition of a coagulating agent thereto, comprising the steps of
    supporting a body of said fluid in a recess having a generally smooth non-wettable inclined surface, introducing a predetermined volume of a coagulating agent into said body to initiate a coagulation reaction, simultaneously drawing a pair of spaced, parallel, and fibrous filaments at the same rate through said body within said recess and in a direction extending upwardly along said inclined surface, and detecting when a clot has formed between said filaments and is moved thereby along said surface.

2. The method of claim 1 in which there is the step of promoting mixing of said fluid and coagulating agent by rotating the filaments about their axes as the same are drawn through said body.

3. The method of claim 2 in which said pair of filaments are rotated in the same direction to produce a counterflow of fluid therebetween.

4. The method of claim 1 in which said filaments are tensioned.

5. The method of claim 1 in which said non-wettable surface is composed of fumed silica microparticles.

6. The method of claim 1 in which said detecting step includes the interruption by said clot of a substantially vertical beam of light passing between said filaments.

7. The method of claim 1 in which there is the further step of stripping said clot from between said filaments by directing said filaments through openings in a barrier wall positioned to block advancement of said clot.

8. The method of claim 7 in which said filaments are lifted away from said recess and are angled downwardly towards said wall during said stripping step.

9. The method of claim 8 in which the velocity of said filaments is increased during said stripping step.

10. The method of claim 1 in which there is the step of guiding said filaments through said recess to maintain constant spacing therebetween.

11. The method of claim 1 in which said recess is provided with a tray having a plurality of such recesses in side-by-side relation, there being the further step of lifting said filaments clear of said tray following clot detection while advancing said filaments to present fresh sections thereof above said tray, simultaneously indexing said tray to position a second of said recesses beneath the fresh sections of said filaments, and thereafter lowering said filaments into said second recess.

12. The method of claim 11 in which the velocity of movement of said filaments is increased during said advancing and indexing steps.

13. The method of claim 1 in which said step of drawing said filaments includes tensioning and restraining the same in advance of said recess to maintain constant velocity thereof.

14. The method of claim 1 in which there is the further step of gently agitating said coagulating agent prior to introducing the same into said body of fluid, said agitating step comprising supporting said agent in a cup and oscillating said cup with respect to a relatively stationary stirring element projecting downwardly therein.

15. A method for determining the coagulation time for a body of clottable fluid supported on a generally smooth non-wettable surface, following the addition of a clotting agent thereto, comprising the steps of
drawing a pair of spaced parallel filaments at the same constant velocity through said fluid body, projecting a beam of light between said filaments, in a generally vertical direction, at a point spaced slightly in front of said body, and timing the interval between the addition of said clotting agent and the interruption of said beam by a clot formed between said filaments and clinging thereto.

16. The method of claim 15 in which said filaments rotate as they are drawn to mix said fluid and coagulating agent.

17. The method of claim 16 in which said filaments rotate in the same direction to produce a counterflow of fluid therebetween.

18. The method of claim 15 in which there is the further step of stripping said clot from between said filaments by directing said filaments over a barrier wall positioned to block movement of said clot.

19. The method of claim 18 in which said filaments are lifted from said surface and are angled downwardly and forwardly towards said wall during said stripping step.

20. The method of claim 19 in which the velocity of said filaments is increased during said stripping step.

21. The method of claim 15 in which there is the further step of lifting said filaments a spaced distance above said surface, following clot formation and the interruption of said beam, while advancing said filaments to present fresh sections thereof above said surface, simultaneously indexing said surface laterally to present a clean portion of the same beneath said filaments, and thereafter lowering said filaments onto said surface.

22. An apparatus for determining the coagulation time of a clottable fluid following the intermixing of that fluid with a clotting agent, comprising a tray having a plurality of recesses in side-by-side relation; each recess having a well portion and a generally smooth non-wettable pathway leading from such well portion; means for supporting the tray in generally horizontal condition; a pair of fibrous filaments; means supporting said filaments in spaced parallel relation with stretches of the same normally extending through said well and along said pathway; and means for slowly advancing said filaments at the same uniform rate; whereby, the interval between the intermixing of said fluid and clotting agent in said well and the movement of a clot from the well and along the pathway, by reason of the bridging attachment of such clot to the moving filaments, is a direct representation of the clotting times of said fluid.

23. The apparatus of claim 22 in which said pathway slopes upwardly and forwardly in the direction of filament movement.

24. The apparatus of claim 22 in which said recess is coated with a superhydrophobic coating of fumed silica microparticles.

25. The apparatus of claim 22 in which said tray is notched at opposite ends of said recess for receiving said filaments and for precisely controlling the spacing therebetween.

26. The apparatus of claim 22 in which said tray is provided with a generally vertical opening intersecting said pathway adjacent said well; said filaments being normally disposed on opposite sides of said opening; and detection means including a light source for projecting a beam of light through said opening and a photocell for detecting when said beam is broken by a clot entrained by said filaments.

27. The apparatus of claim 22 in which each tray is provided with an upstanding barrier wall adjacent the end of each pathway opposite form said well; and a trough interposed between said wall and said pathway; said wall being provided with a pair of notches through which said filaments extend; whereby as said filaments advance, a clot entrained by said filaments is stripped therefrom by said wall and is collected in said trough.

28. The apparatus of claim 22 in which said means for supporting said filaments includes a guide arm movable between a lowered first position, an inclined second position, and a raised third position; means mounting said arm for movement between each of said positions; and guide elements mounted upon said arm for supporting said filaments and guiding movement thereof; said stretches of filaments extending through said well and along said pathway only when said arm is in said first position, and being spaced substantially above said tray when said arm is in said third position.

29. The apparatus of claim 28 wherein said tray is arcuate in configuration; said means for supporting said tray comprising a turntable; and power means for indexing said turntable for successively positioning each of said recesses beneath said filaments when said arm is raised into its third position.

30. The apparatus of claim 28 wherein said tray is provided with an upstanding barrier wall adjacent the end of each pathway opposite from said well; a trough interposed between said well and said pathway; said wall being provided with a pair of notches through which said filaments extend; said filaments being spaced above said wall and said pathway, and engaging said tray only at said wall, when said arm is in its second position; whereby, as said filaments are advanced while said arm is in its second position a clot entrained by said filaments is stripped therefrom by said wall and is collected in said trough.

31. The apparatus of claim 28 in which said means for slowly advancing said filaments includes a pair of power-operated take-up reels, slip clutch means associated with said reels, and capstan engaging said filaments in advance of said tray, said capstan being power driven at a constant peripheral speed slower than the minimum peripheral speed of said take-up reels.

32. The apparatus of claim 31 in which means are provided for holding said filaments in tight engagement with said capstan only when said arm is in said first position; whereby, when said arm is in said second and third positions, said filaments advance at an increased rate established by said take-up reels without the restraining influence of said capstan.

33. The apparatus of claim 32 in which said means for holding said filaments in tight engagement with said capstan when said arm is in said first position comprises a resilient roller, and means interconnecting said roller and arm for synchronizing movement therebetween.

34. The apparatus of claim 22 in which said means for slowly advancing said filaments includes a pair of upper and lower take-up reels removably supported at the upper ends of a pair of concentric power-driven shafts; a drip pan beneath said reels; said reels and pan being connected together against axial separation while being rotatable relative to each other.

35. The apparatus of claim 34 in which said upper reel is provided with a handle for removal of said reels and drip pan as a unitary assembly from said shafts.

36. The apparatus of claim 35 in which said reels and drip pan are formed of plastic material.

37. The apparatus of claim 22 in which means are provided for supporting and agitating said clotting agent to maintain the same in condition for addition to said fluid; said means comprising a cup, means supporting said cup and oscillating the same in a horizontal plane, and a transfer pipette adapted to project into the contents of said cup and remain relatively motionless as said cup is oscillated.

38. The apparatus of claim 22 in which said means for supporting said filaments includes a guide arm having lateral guide bars projecting therefrom and engaging said filaments for supporting and guiding the same; said filaments each being composed of a multiplicity of fibers twisted together and having free ends projecting outwardly from such filament; and means for maintaining said filaments in a state of tension; said bars imparting a rotational action to said twisted and tensioned filaments as said filaments are advanced.

39. The apparatus of claim 22 in which means are provided for spacing said filaments a slight distance above the surface of said well and pathway.

40. The apparatus of claim 25 in which the notches at opposite ends of said recess have their lower ends terminating above the bottom surface of said recess to space said filaments slightly above said surface.

* * * * *